United States Patent [19]

Biro et al.

[11] Patent Number: 5,133,730

[45] Date of Patent: Jul. 28, 1992

[54] DISPOSABLE-RETRACTABLE FINGER STICK DEVICE

[75] Inventors: Ladislau Biro, Metuchen; Robert F. Cusack; Michael D. Mintz, both of Edison, all of N.J.

[73] Assignee: International Technidyne Corporation, Edison, N.J.

[21] Appl. No.: 700,592

[22] Filed: May 15, 1991

[51] Int. Cl.$^5$ .............................. A61B 17/32
[52] U.S. Cl. ..................................... 606/182
[58] Field of Search ..................... 606/167, 181–183

[56] References Cited

U.S. PATENT DOCUMENTS

| | | | |
|---|---|---|---|
| 4,230,118 | 10/1980 | Holman et al. | 606/182 |
| 4,414,975 | 11/1983 | Ryder et al. | 606/182 |
| 4,539,988 | 9/1985 | Shirley et al. | 606/182 |
| 4,628,929 | 12/1986 | Intengan et al. | 606/182 |
| 4,892,097 | 1/1990 | Ravalletta et al. | 606/182 |

*Primary Examiner*—Max Hindenburg
*Attorney, Agent, or Firm*—Arthur L. Plevy

[57] ABSTRACT

A finger stick device for making a skin incision includes a blade pivot arm having a first end pivotally coupled to a housing and a second end having an upper sloped surface and a lower surface. A blade is affixed to the second end such that its cutting edge extends away from the lower surface. A resilient bias member when actuated traverses the upper surface and depresses the second end of the blade pivot arm, such that the blade exits the housing and incises the skin. The incising operation is complete upon the bias member traversing the sloped upper surface of the blade pivot arm. Also disclosed herein is a method for manufacturing the finger stick device, in which the bias member and blade pivot arm are molded as a monolithic unit. A blade is attached to the blade pivot arm, and the blade and monolithic unit are inserted into the housing. Further disclosed is an embodiment in which the housing is formed of two uniformly shaped halves, which when joined, provide an internal space for the monolithic unit. In this manner, the two halves are joined with the monolithic unit aligned therebetween so that the housing appears as an integral unit.

23 Claims, 8 Drawing Sheets

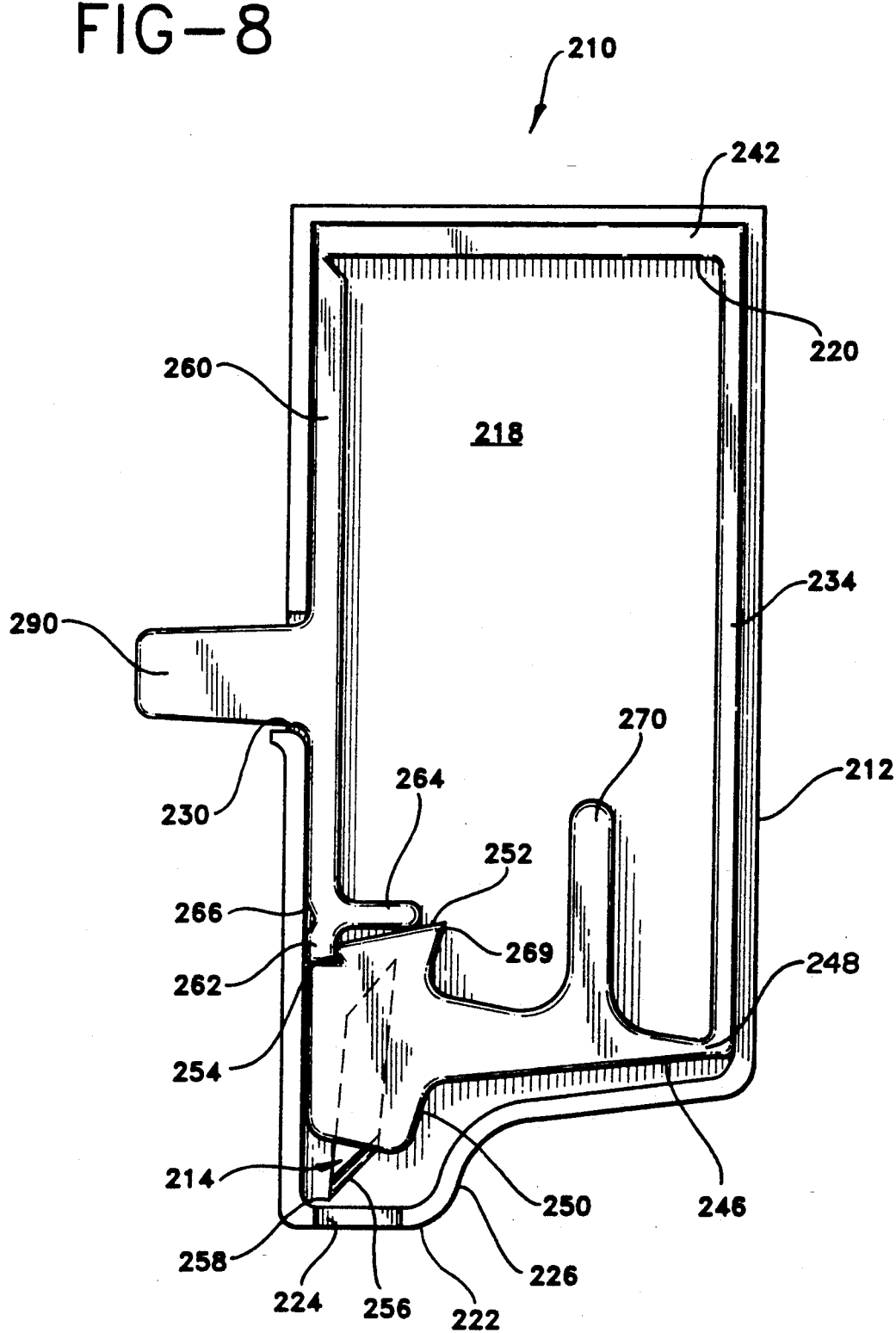

DISPOSABLE-RETRACTABLE FINGER STICK DEVICE

BACKGROUND OF THE INVENTION

The invention relates generally to apparatus for producing a skin incision in order to cause bleeding and to a method for making such apparatus, and more particularly to a disposable finger stick device capable of producing an incision.

Blood samples are drawn routinely from patients for use in various types of blood tests. The blood is usually taken from an appropriate area, such as the patient's fingertip. A series of mechanical devices for producing skin incisions necessary to draw blood samples have been developed. One such device is a reusable mechanical device that has a disposable blade. To its advantage, the mechanical device prevents the patient from seeing the often unsettling scene of his skin being cut. Further, the mechanical device provides good control of the incision. However, handling of the blades during disposal presents a danger. There is the danger of being cut by the exposed edge. Further, the health problems posed by used blades are apparent. More recent health considerations, including the possibility of contracting the AIDS virus from disposed blades, have increased the need for safer devices.

Disposable devices that produce standardized skin incisions were developed to overcome the problem caused by disposable blades. For instance, the device disclosed in U.S. Pat. No. 4,078,552, entitled "DEVICE FOR AND METHOD OF MAKING STANDARD AND REPRODUCIBLE SKIN PUNCTURES", issued to Evan N. Chen on Mar. 14, 1978 and assigned to Warner-Lambert Company, has a housing and a blade located inside the housing. The blade is supported by a post, which is surrounded by a spring. When a release mechanism associated with the housing is activated, the spring pushes the blade in a downward thrust, much like the action of a guillotine, and hence the blade penetrates the patient's skin, thereby making a puncture. The blade is not retractable, which causes two major drawbacks. First, the blade, once activated to penetrate the skin of a patient, remains within the patient's skin until the housing is pulled away. Therefore, the blade is in the patient's skin for a period longer than necessary, thereby causing unnecessary pain. Second, the blade, once removed from the patient's skin, is still exposed to the technician and patient, and therefore presents the same handling and health problems indicated above.

The "LANCET" disclosed in U.S. Pat. No. 4,677,979, issued to James Burns on Jul. 7, 1987 and assigned to Becton, Dickson and Company, has essentially the same structure as the device disclosed in the Chen reference, the difference being that the release mechanism includes a plunger that depresses the spring-like mechanism, and that a resilient member is located between the plunger and the housing. When the plunger is released, the resilient member forces the plunger upwards, causing the blade to be removed from the patient's skin and withdrawn into the housing. However, the problem relating to the exposed blade is not entirely overcome, since the plunger can be reactuated and the blade can be directed from the housing again. This operation can cause a contaminated blade to be inserted into the skin of another person. Furthermore, the problem attributed to unnecessary pain is not overcome, since the blade is not removed from the patient' skin until the plunger is released.

U.S. Pat. No. 4,735,203, entitled "RETRACTABLE LANCET", issued to Francis E. Ryder and Harold L. Purdy on Apr. 5, 1988 and assigned to Ryder International Corporation, appears to avoid that problem. The RETRACTABLE LANCET includes a housing having an open end, a carrier, which is mounted in the housing for a sliding motion toward and away from the open end, and a blade which is affixed to a carrier. A resilient biasing member is mounted in the housing in a prestressed condition and is operatively coupled for selectively urging the carrier toward and away from the housing open end. A non-resettable release member normally retains the biasing member in its prestressed condition and is selectively activated for releasing the resilient bias member, which sets the carrier into motion. The cutting edge of the blade is projected through the opening and makes a downward thrust which punctures the patient's skin. Immediately following the downward thrust is a movement which includes a retraction of the entire blade into the housing. Thus, the blade performs the incision and then is retracted back into the housing to enable safe disposal of the unit.

Essentially, the incisions produced by the above-noted prior art devices are made by a downward thrust into the skin. Further, there may be a problem of excessive force being applied to the skin, which can cause skin tissue to be damaged. Generally, only a small amount of downward force is required to make the incision. However, when the operator actuates the device, his hand may exert an additional, and often excessive, downward force. Thus, the guillotine-like, vertical thrust of the blade, coupled with excessive downward force exerted by the operator may cause damage to the skin and cause skin tissue juices to mix with blood. This mixing provides improper blood samples.

The "APPARATUS FOR IMPLEMENTING A STANDARDIZED SKIN INCISION" disclosed in U.S. Pat. No. 4,643,189, issued to Michael Mintz on Feb. 17, 1987 and assigned to W.T. Associates, includes a housing having an internal hollow and a base containing an elongated slot. The internal hollow contains a movable pivot arm having a first pivotal end and a second end having a cam follower. There is a cam surface upon which the cam follower of the pivot arm rides. The pivotal end of the arm includes a cutting edge, which moves transversely while the arm is pivoting. The cam controls the path of the cutting edge as it enters the slot. After the unit is triggered, the edge projects through the slot in the housing along a given path to implement the incision. After traversing the path, the cutting edge is withdrawn into the housing to prevent further use and injury. Thus, this retractable-disposable device has a rapid action that produces a scalpel-like incision of standard length. Furthermore, the device is fabricated from molded plastic and simple metal parts, which makes manufacture simple and economical.

It is an objective of the present invention to provide a reliable and safe device that produces a predetermined incision and that can operated with minimum effort.

It is a further objective of the present invention to provide a method of manufacturing such a device at a reasonable cost.

SUMMARY OF THE INVENTION

The present invention relates to a retractable-disposable finger stick device for making an incision in the tip of a patient's finger in order to draw a small amount of blood. The finger stick device includes a blade having a cutting edge, housing means, having a surface adapted to be placed flush against the skin, for housing the blade and blade pivoting means, located within the housing means, for pivotally guiding the blade through an elongated slot in the surface. A first end of the blade pivoting means is pivotally coupled to the housing means. The second end of the blade pivoting means has an upper surface and a lower surface. The blade is affixed to the second end such that its cutting edge extends away from the lower surface. The upper surface of the second end is sloped. The finger stick device further includes depressing means, which traverses the sloped upper surface, for depressing the second end of the pivoting means, such that the blade moves in an arcuate motion, in which its cutting edge traverses the elongated slot and incises the skin. The incising operation is complete after the depressing means traverses the sloped upper surface.

The present invention further relates to a method for manufacturing the finger stick device, which method includes the steps of (a) providing a case having an internal hollow, an open end and an elongated slot at the opposite end of the case; (b) molding a monolithic trigger mechanism including support means, blade pivoting means for pivotally guiding a blade, the blade pivoting means having a first end which is pivotally attached to the support means and a second end having an upper surface and a lower surface, the upper surface being sloped, and depressing means for depressing the upper surface of the second end of the pivoting means; (c) attaching a blade to the second end of the blade pivoting means such that its cutting edge extends away from the lower surface; (d) inserting the monolithic trigger mechanism through the open end of the case; (e) attaching the support means to the case; and (f) covering the open end of the case.

BRIEF DESCRIPTION OF THE DRAWINGS

FIG. 8 is a cross-sectional view of a third embodiment of a finger stick device.

DETAILED DESCRIPTION OF THE EXEMPLARY EMBODIMENTS

Figure 1:
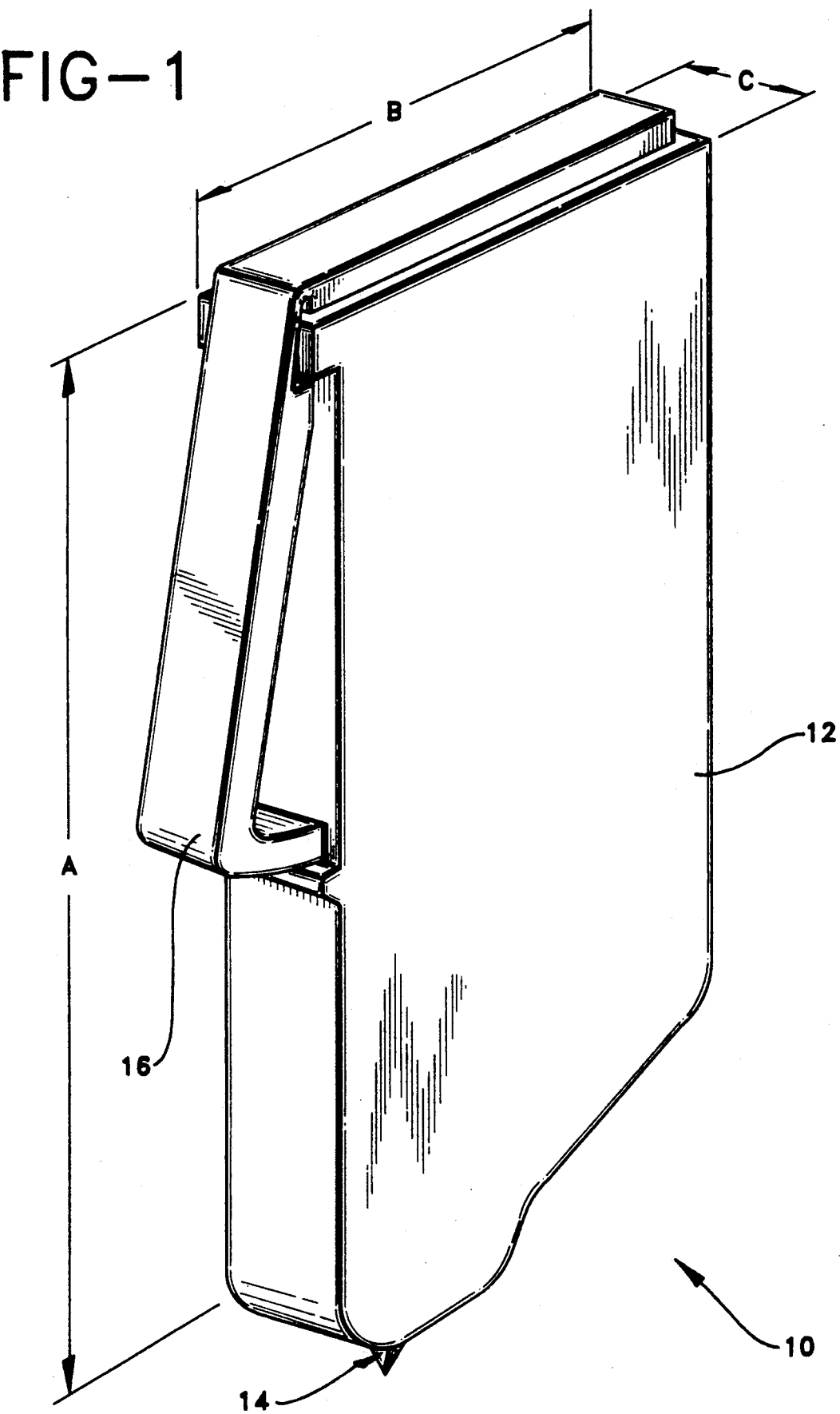
FIG. 1 is a perspective view of a finger stick device in accordance with the present invention.

Referring to FIG. 1, there is shown a finger stick device 10 for performing a skin incision according to the present invention. The visible elements of the finger stick device 10 include a housing 12, a blade 14, which is partially enclosed by the housing 12, and a lever arm 16, which protrudes from the housing 12. In order to gain some insight into the size of the finger stick device 10, it should be understood that the housing 12 must be grasped by the hand of an operator. Typical dimensions for the housing 12 include an overall length A of 2 inches, a width B of 1 inch and a thickness C of ¼ inch. The dimensions can vary, of course, but as one can ascertain, the finger stick device 10 is relatively small. The operator holds the finger stick device 10 with one hand such that the housing is firmly grasped at its sides between the thumb and middle finger while the index finger rests against the lever arm 16. The operator firmly places the bottom surface flush against the patient's skin at the location where incision is desired, and squeezes the lever arm 16. The depression of the lever arm 16 irreversibly actuates a finger stick mechanism, which is located within the housing 12. The finger stick mechanism causes the blade 14 to exit the housing and to puncture the patient's skin, and immediately thereafter, to retract into the housing 12. Once depressed, the lever arm 16 cannot reactuate the finger stick mechanism; therefore, the blade 14, once used, is locked permanently within the housing 12.

Figure 2:
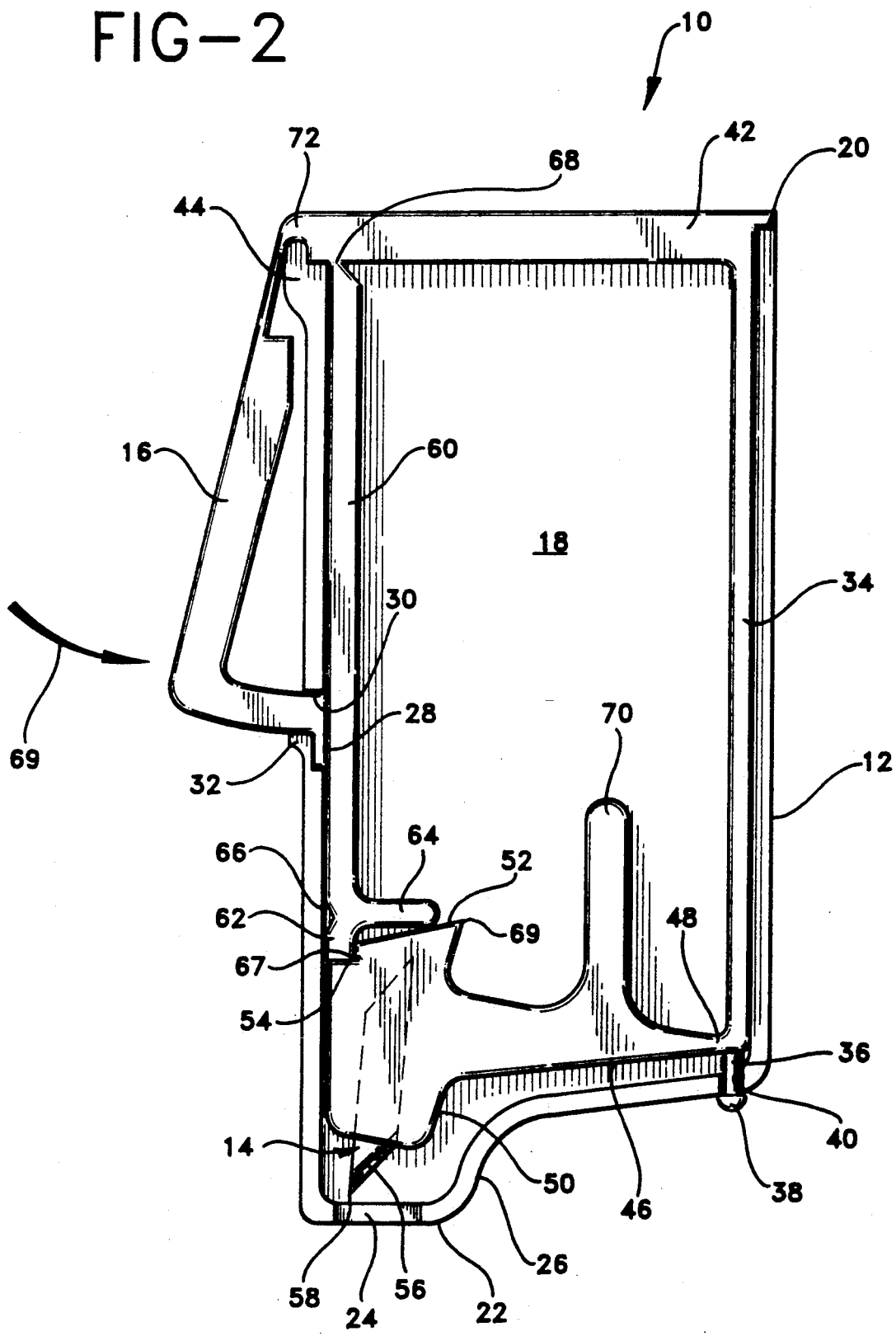
FIG. 2 is a cross-sectional view of the finger stick device illustrated in FIG. 1, taken in its quiescent state.

Referring now to FIG. 2, there is shown a cross-sectional view of the finger stick device 10 in its quiescent state. The housing 12, which is elongated, has an internal hollow 18, an open end 20, which provides access to the internal hollow 18, and a closed end, which forms a base 22. A longitudinal slot 24 is located in the base 22. The blade 14 traverses the longitudinal slot 24 on the base 22 and makes the incision. Since the exact position of the longitudinal slot 24 on the base 22 is obscured from the operator, he may have trouble determining where on the patient's skin, the device 10 must be located in order to make the incision. Thus, the portion 26 of the base 22 containing the longitudinal slot 24 is made to extend away from the housing 12. This portion 26 serves to indicate to the operator the position of the longitudinal slot 24 with respect to the skin of the patient.

The lever arm 16, which is L-shaped, has a first end that is pivotally coupled to the housing 12 near its open end 20 and a second end, which terminates in a catch 28. The catch 28 extends through a first aperture 30 located in the housing 12 and is received by a ridge 32 in the housing 12, which ridge 32 functions to prevent the second end of the lever arm 16 from being withdrawn from the housing 12.

The components of the finger stick mechanism are contained within the internal hollow 18 of the housing 12. A vertical reference member 34 has one end that terminates in a projecting pin 36. A one way lock, such as a resilient projection 38, is located at the tip of the projecting pin 36. The projecting pin 36 and projection 38 extend through a second aperture 40 located on the base 22 of the housing 12, and function to secure the vertical reference member 34 to the housing 12. The opposite end of the reference member 34 terminates in a horizontal reference member 42 that also serves as a cover, which is received by a channel 44 located at the open end 20 of the housing 12. The horizontal reference member 42 functions to seal the open end 20 of the housing 12 and is thereby secured to the housing 12. The vertical reference member 34 and horizontal reference member 40 comprise a support structure that is secured to the housing 12, thus, providing mechanical coupling between components joined to the vertical reference member 34 or the horizontal reference member 42 and the housing 12.

A blade pivot arm 46 has one end that is pivotally attached to the vertical reference member 34 by a first living hinge 48. The opposite end of the blade pivot arm 46 terminates in a blade holder 50. At the upper surface of the blade holder 50 is a ramp 52, which has a positive slope. A detent 54 is located at the base of the ramp 52. The blade 14, which includes a cutting edge 56 and a sharpened apex 58, is coupled to the blade holder 50 such that the cutting edge 56 extends towards the longitudinal slot 24. Scalpel-like in function, the blade 14 produces an incision required by the present invention. Thus, when the blade pivot arm 46 is pivoted, the blade 14 traverses the longitudinal slot 24 and makes an incision in the patient's skin.

A bias member 60, which is elongated, has one end that terminates in two legs, one of which is a push rod 62 and the other of which is a pawl 64. A notch 66 is located above the push rod 62. The opposite end of the bias member 60 is pivotally attached to the horizontal reference member 42 by a second living hinge 68, such that the bias member 60 is abutted against, but not attached to, the catch 28 of the lever arm 16 and such that a projection 67 on the push rod 62 is received by the detent 54. When the projection 67 is received by the detent 54, the first living hinge 48 is axially prestressed, which causes the blade pivot arm 46 to lock in place.

Figure 3:
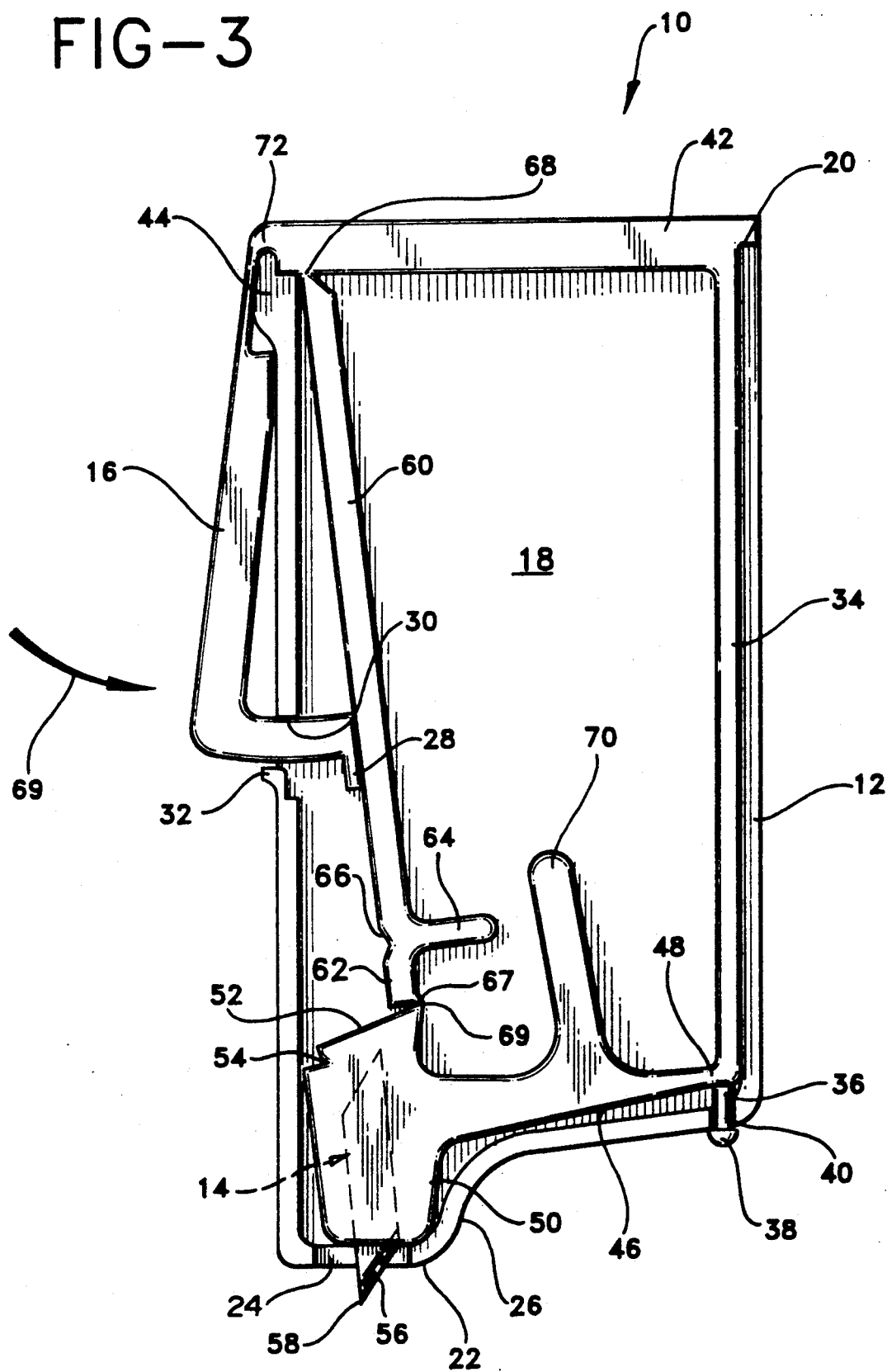
FIG. 3 is a cross-sectional view of the finger stick device illustrated in FIG. 1, taken while the blade is making an incision.

The bias member 60 must be made of a resilient material and must have a thickness that allows it to flex without snapping. When the lever arm 16 is depressed in the direction of the arrow 69, its catch 28 pushes against the bias member 60. Because the projection 67 is engaged with the detent 54, the bias member 60 flexes, which causes it to store energy. This stored energy, when released, is channeled to depress the blade holder 50. As the bias member 60 is flexed, its effective length decreases to cause the blade support arm 46 to pivot upward. The flexure of the bias member 60 also causes the pawl 64 to engage the top surface of the ramp 52. The pawl 64 depresses the ramp 52 to cause the projection 67 to disengage from the detent 54. Once disengaged, the flexed bias member 60 simultaneously unflexes and pivots about living hinge 68, causing the push rod 62 to rapidly traverse the ramp 52. As a result of these actions, the push rod 62 irreversibly traverses the ramp 52, thereby depressing the blade holder 50 and causing it to pivot about the vertical reference member 34 (See FIG. 3). As the blade 14 is pivoted, its cutting edge 56 moves transversely through the longitudinal slot 24 and incises the patient's skin, until the blade pivot arm 46 abuts against the extended portion 26 of the housing 12. Thus, the blade 14, while under the influence of the bias member 60, makes an incision at a relatively predetermined depth sufficient to incise blood vessels, such that a blood sample can be drawn from the patient.

The incising operation of the finger stick device 10 is extremely rapid thereby reducing the patient's sensation of pain. Once the lever arm 16 is depressed, the bias member 60 is irreversibly actuated, in which its snap-action depresses the blade pivot arm 46. The cutting edge 56 traverses the longitudinal slot 24 in an extremely short period of time (1-5 milliseconds). The duration of the incising operation is determined by the length of the ramp 52 and the elasticity and flexure of the bias member 60. The depth of the incision is determined by the position of the blade 14 relative to the lower surface of the portion 26 of the housing 12 when the blade pivot arm 46 has been fully pivoted until the blade holder 50 abuts against the inner surface of the extended portion 26 of the housing 12. For this further reason, the portion 26 of the base 22 is positioned to confine (limit) the motion of the blade pivot arm 46. Further, the length of the pawl 64 determines the amount of energy that is stored by the bias member 60. If the pawl 64 is elongated, there is little flexure in the bias member 60 before the projection 67 is caused to disengage from the detent 54. Because little energy is stored in the bias member 60, the bias member 60 cannot snap across the ramp 52. Therefore, the lever arm 16 is required to push the bias member 60 across the ramp 52. Thus, the operator, by depressing the lever arm 16, controls the speed at which the incision is made. Conversely, if the length of the pawl 64 is made short, there is considerably more flexure before the projection 67 is caused to disengage from the detent 54. Thus, a greater amount of energy is stored in the bias member 60 and is available to accelerate the push rod 62 as it irreversibly snaps across the ramp 52. This is the desired operation.

Located on the blade pivot arm 46, intermediate its ends, is a lift lever 70, which extends towards the open end 20 of the housing 12. The lift lever 70 functions to help retract the blade 14 into the housing 12. Immediately after the push rod 62 traverses the ramp 52, the pawl 64 strikes the lift lever 70, whereupon blade pivot arm 46 reverses direction and pivots the blade 14 into the housing 12. This retraction of the blade 14 is aided by the plastic memory of the first living hinge 48. Thus, immediately after the incision is implemented, the blade is caused to retract into the housing 12.

Figure 4:
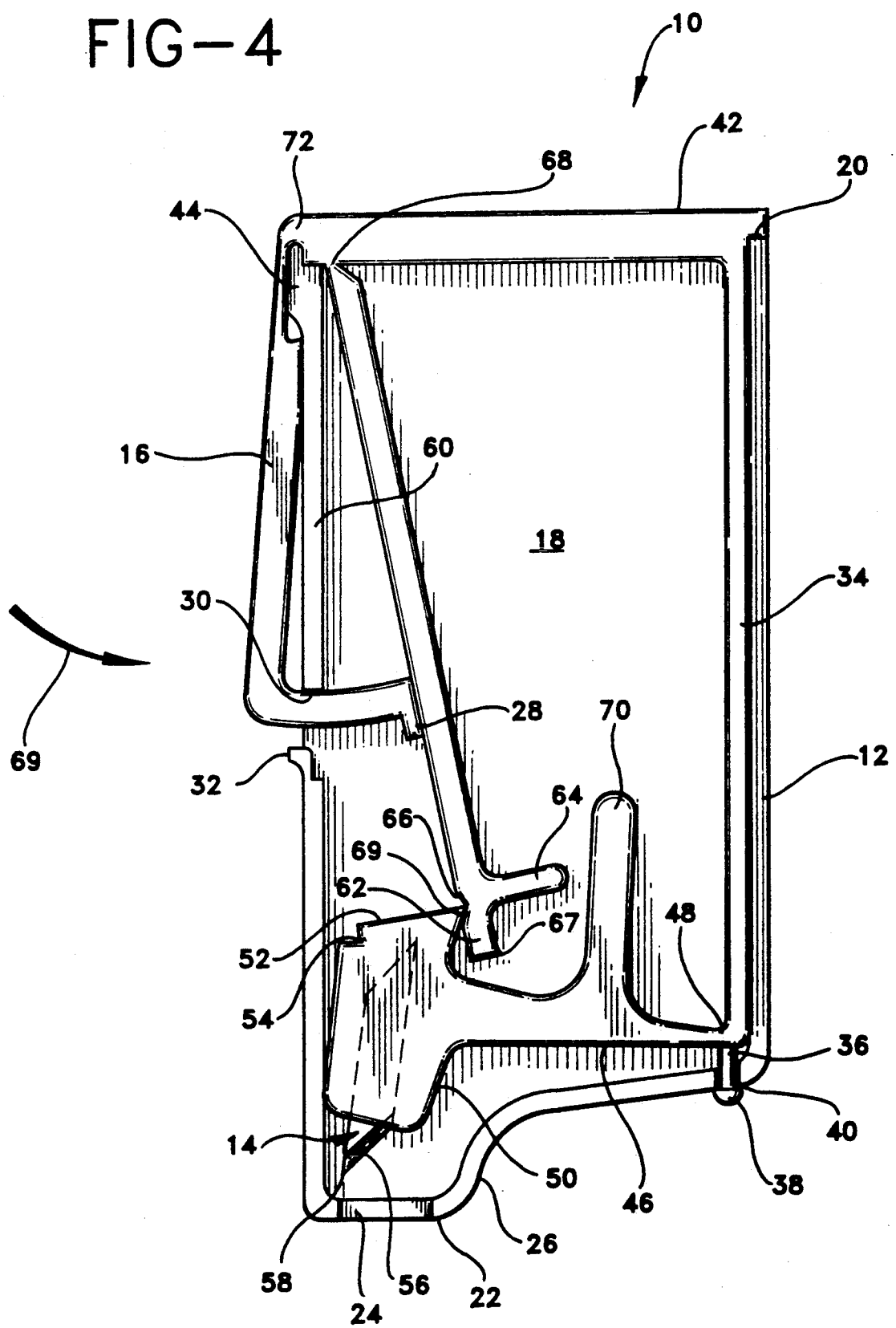
FIG. 4 is a cross-sectional view of the finger stick device illustrated in FIG. 1, taken after the finger stick mechanism was actuated.

At the point where the pawl 62 and the lift lever 70 collide, the bias member 60 has expended most of its stored energy. Due to this loss of energy, and due to the plastic memory of the second living hinge 68, the bias member 60 begins to pivot back to the quiescent position, whereupon the notch 66 engages the tip 69 of the ramp 52, thereby locking the blade pivot arm 46 in a final, stationary position (see FIG. 4). The plastic memory of the second living hinge 68 urges the bias member 60 against the tip 69 of the ramp 52 on the blade holder 50. Thereafter, the lever arm 16 cannot extend into the housing 12 far enough to disengage the bias member 60 from the ramp 52, and the blade 14 is permanently locked within the housing 12.

Figure 5:
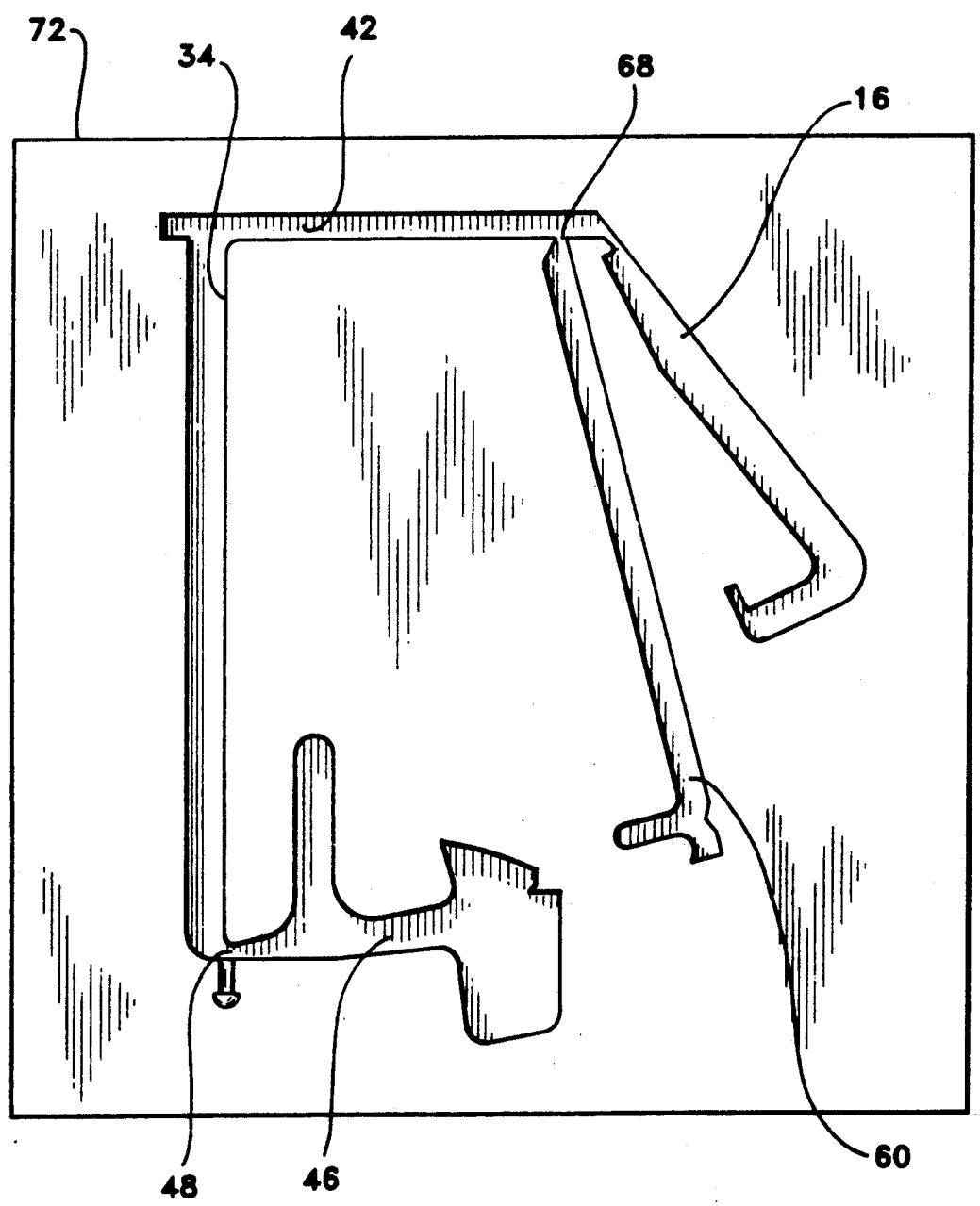
FIG. 5 is a top plan view of a mold cavity for a finger stick mechanism, which finger stick mechanism forms a part of the finger stick device illustrated in FIG. 1.

The finger stick mechanism does not have to be formed integrally, but rather can be assembled from the separate components 16, 34, 42, 46 and 60. However, to enjoy the significant advantages in fabrication and assembly offered by the finger stick device 10 according to the present invention, the vertical reference member 34, horizontal reference member 42, bias member 60, blade pivot arm 46 and lever arm 16 are formed integrally in a single mold cavity 72 (see FIG. 5) from a resilient material, such as polypropylene plastic. The first and second living hinges 48 and 68 are formed by reduced cross sections of connecting members: bias member 60 to horizontal reference member 42; and blade pivot arm 46 to vertical reference member 34, respectively.

When the finger stick mechanism and lever arm 16 are integrally formed, the assembly of the finger stick device 10 is made simple. First, the blade 14 is attached to the blade holder 50 by conventional means. Then, by rotating bias member 60 and blade pivot arm 46, the projection 67 of the push rod 62 is caused to engage the detent of the blade pivot arm 46. The finger stick mechanism and blade 14 are then inserted into the internal hollow 18 of the housing 12, such that the projecting pin 36 is inserted into the second aperture 40, whereby the resilient projection 38 locks the vertical reference member 34 to the housing 12, such that the horizontal reference member 42 is received by the channel 44 in the housing 12, whereby the open end of the housing 12 is sealed, and such that the projection 67 of the push rod 62 remains in contact with detent 54 on the blade pivot arm 46. Thus, it can be appreciated that the vertical reference member 34 and horizontal reference member 42 function to locate the bias member 60 and blade support arm 46 within the housing, such that the projection 67 of the push rod 62 engages the detent 54. The lever arm 16 is wrapped around the lip 72 of the open end 20 of the housing 12. To complete the assembly of the finger stick device 10, the catch 28 on the lever arm 16 is clipped onto the ridge 32 on the housing 12. When the finger stick mechanism is properly inserted in the housing 12, the blade 14 is aligned with the longitudinal slot 24. Assembled as such, the cutting edge 56 of the blade 14 is located completely within the housing 12 of the finger stick device 10 and is not exposed in any manner whatsoever until the finger stick mechanism is actuated.

Thus described is a finger stick device 10 which rapidly makes an incision, and then retracts the blade 14 into the housing 12. The lever arm 16 is depressed in a direction transverse to the skin of the patient, which allows for triggering of the finger stick device without having to press harder on the patient's skin. Once the lever arm 16 is depressed, the operation is irreversible; the snap-like action of the bias member 60 traverses the ramp 52 in a matter of milliseconds. Once the operation has ended, the bias member 60 can no longer be reactuated, thereafter making the finger stick device 10 unusable. As a result, there is no danger in disposing the finger stick device 10 since the blade 14 is permanently and completely stored within the housing 12. A further advantage lies with the ease of manufacturing the finger stick device 10. The finger stick device 10 consists of three inexpensive components—a housing 12, a finger stick mechanism and a blade 14—that can be assembled quickly, easily and inexpensively. The simplicity of design and assembly makes the manufacture advantageous over the prior art.

Figure 6:
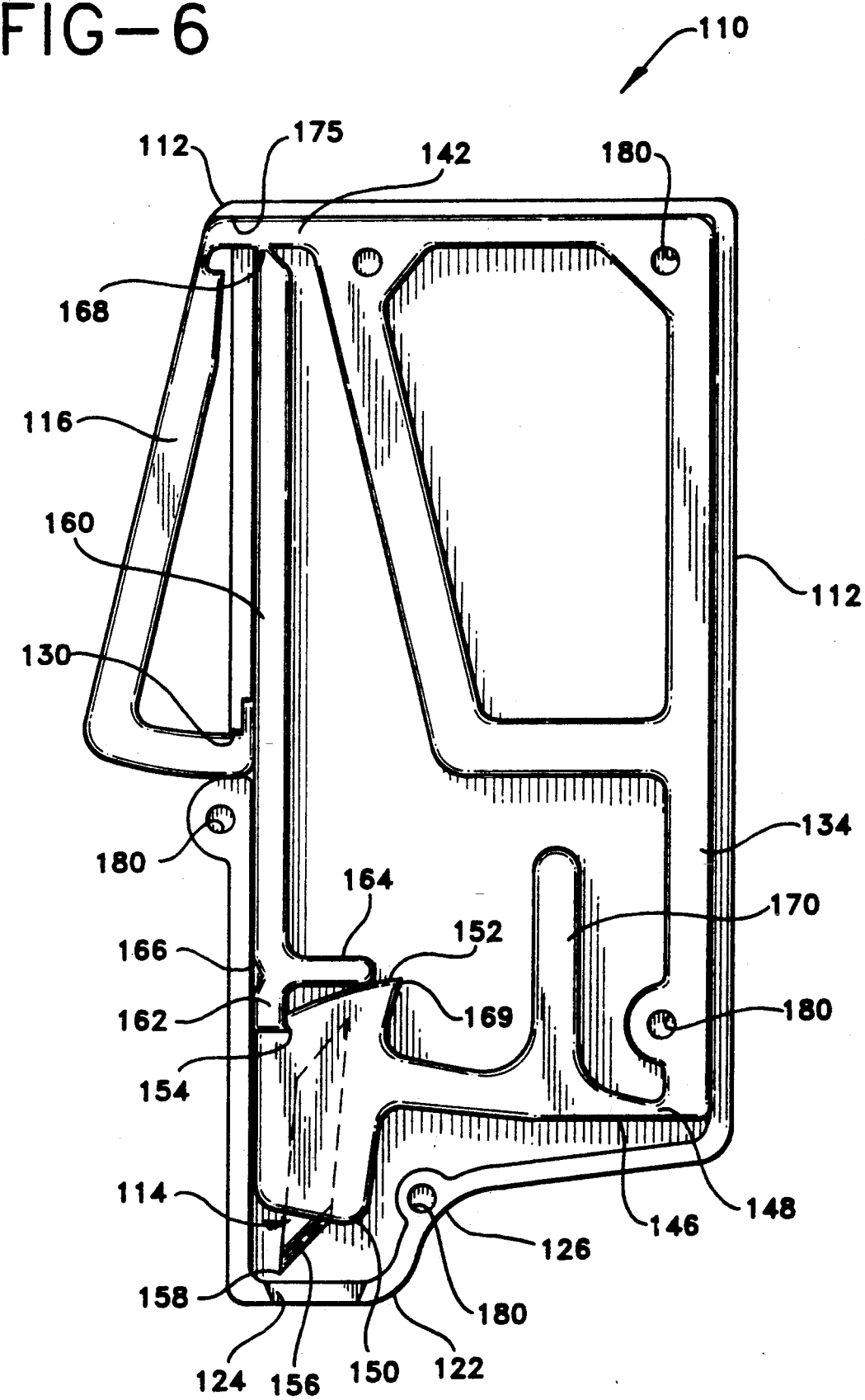
FIG. 6 is a cross-sectional view of a second embodiment of a finger stick device mechanism being shown in the left half of the case.
Figure 7:
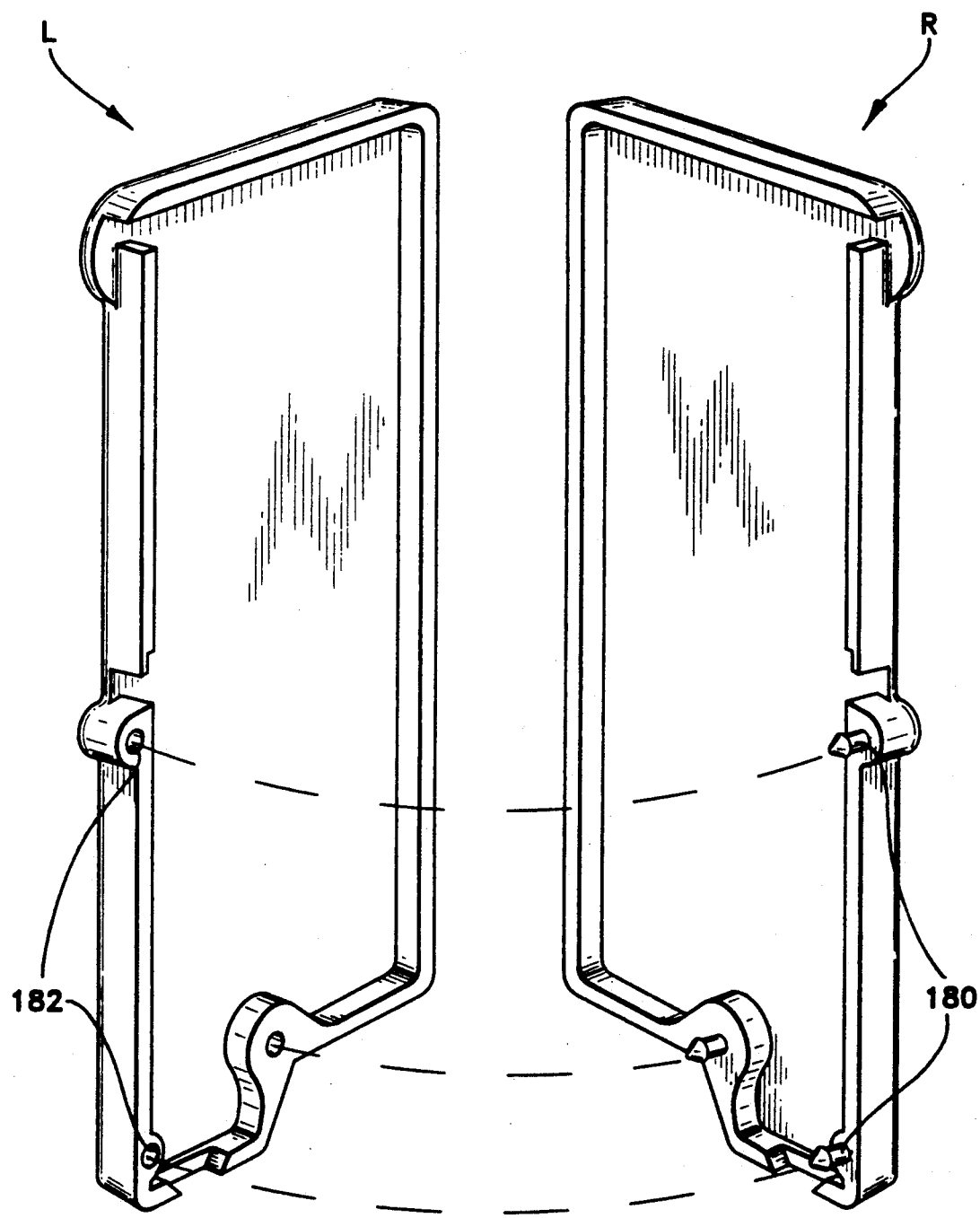
FIG. 7 is a perspective view of the second embodiment and the corresponding halves that are joined to form the housing into an integral unit.

A second embodiment in accordance with the present invention is illustrated in FIGS. 6 and 7. Elements illustrated in FIGS. 6 and 7 that correspond to the elements described above with respect to the embodiment illustrated in FIGS. 1-5 have been designated by corresponding reference numerals increased by one hundred. Unless otherwise stated, the embodiment illustrated in FIGS. 6 and 7 operates in the same manner as the embodiment illustrated in FIGS. 1-5.

Referring now to FIGS. 6 and 7, there is shown a second embodiment of the present invention. The housing means 112 comprises a left half "L" and a right half "R". For clarity the mechanism is not shown in FIG. 7 for this embodiment. The right half R has locator pins 180 while the left half L has locator holes 182 (FIG. 7). Also, the left and right halves are each grooved so that when the halves are joined, an aperture 175 (FIG. 6) is formed at the grooves. The aperture is located in the housing means 112 at an end opposite that of the longitudinal slot 124 and in proximity to where the lever arm 116 is pivotally coupled to the horizontal reference member 142. The aperture 175 permits the lever arm 116 to extend from the housing means 112. In this embodiment, each one of the locator pins 180 is received in a corresponding locator hole 182 for locating the right half R of the case to fit onto the left half L of the case. When joined, the left and right halves form the housing means 112 as an integral unit. The locator pins and holes also align the finger stick mechanism within the housing means 112. When manufacturing the device, the finger stick mechanism is placed between the left and right halves and then the two halves are brought together. In this configuration, the mechanism is completely contained and properly aligned within the housing 112. The embodiment shown in FIGS. 6 and 7 is different from the first embodiment shown in FIGS. 1-4. The difference is that the first embodiment has an open top through which the finger stick mechanism is inserted before closing the open top with a cover. In the second embodiment, there is no open top through which the mechanism is to be inserted, but rather, the mechanism is placed between the left and right halves of the housing means (FIG. 7) after which the left and right halves are joined by each one of the locator pins 180 being inserted into a corresponding one of the locator holes 182. This configuration comprises parts that are simpler to mold and assemble, off-setting the inconvenience of one additional part, as compared to the previously described embodiment. Therefore, the second embodiment is the preferred embodiment of the present invention.

It will be understood by one skilled in the art that the attachment functions of the locator pins 180 and locator holes 182 may be achieved by other mechanisms such as grooves and undercuts at the join line of the left and right halves of the housing means 112. It will be further understood that grooves or projections molded into the left and/or right halves of the housing means 112 may be employed to align the finger stick mechanism within the housing means 112.

A third embodiment in accordance with the present invention is illustrated in FIG. 8. Elements illustrated in FIG. 8 that correspond to the elements described above with respect to the second embodiment illustrated in FIGS. 6 and 7 have been designated by corresponding reference numerals increased by one hundred. Unless otherwise stated, the third embodiment illustrated in FIG. 8 operates in the same manner as the second embodiment illustrated in FIGS. 6 and 7.

Referring now to FIG. 8, there is shown a third embodiment of the present invention. A push button 290 extends from the lever arm 260. The push button 290 obviates the need for having an upper aperture 175 at the front of the housing 212. When the push button 290 is depressed, the finger stick mechanism is activated. This embodiment may be assembled in a similar manner as that disclosed with reference to FIGS. 6 and 7.

It will be understood that the embodiments described herein are merely exemplary and that a person skilled in the art may make many variations and modifications without departing from the spirit and scope of the invention. All such modifications are intended to be included within the scope of the invention as defined in the appended claims.

We claim:

1. Apparatus for implementing a skin incision, comprising:
   a blade having a cutting edge;
   housing means for housing said blade, said housing means having an exterior surface adapted to be placed flush against the skin and an elongated slot located on said exterior surface;
   blade pivoting means, located within said housing means, for pivotally guiding said blade through said elongated slot, said blade pivoting means having a first and second end wherein said first end is pivotally coupled to said housing means and said second end supports said blade, whereby said cutting edge extends from a first surface of said second end toward said elongated slot, said second end having a sloped surface formed thereon opposite said first surface; and
   actuatable depressing means, located within said housing means, for engaging and holding said blade pivoting means in a set position, preventing the pivotal movement of said blade pivoting means within said housing, said depressing means being actuated to disengage said blade pivoting means and transverse said sloped surface, displacing said second end of said blade pivoting means toward said elongated slot, such that said cutting edge of said blade emerges from said elongated slot and incises the skin.

2. An apparatus according to claim 1, wherein said depressing means includes an elongated member having a first end that is pivotally coupled to said housing means and a second end that abuts against and displaces said sloped surface of said second end of said blade pivoting means when said depressing means is actuated.

3. An apparatus according to claim 2, wherein said blade pivoting means further includes engaging means for engaging said second end of said elongated member such that said blade is located at said set position entirely within said housing means before said depressing means is actuated.

4. An apparatus according to claim 3, wherein said engaging means includes a detent, located at said second end of said blade pivoting means, for receiving said second end of said elongated member.

5. An apparatus according to claim 3, wherein said blade pivoting means includes a living hinge, located at said first end of said blade pivoting means, and which pivotally couples said first end of said blade pivoting means with respect to said housing.

6. An apparatus according to claim 4, wherein said elongated member is resilient, and wherein said depressing means is actuated by flexing said elongated member to cause said second end of said elongated member to disengage said detent and to traverse said sloped surface of said blade pivoting means at a rate according to the amount of flexure of said elongated member.

7. An apparatus according to claim 6, wherein said depressing means further includes disengaging means for disengaging said second end of said elongated member from said detent according to the amount of flexure of said elongated member.

8. An apparatus according to claim 7, wherein said disengaging means is pawl adjacent to said second end of said elongated member, which pawl contacts said sloped surface of said blade pivoting means when said depressing means is actuated so as to pivot and disengage said second end of said elongated member from said detent, said pawl having a predetermined length to control the amount of lexure of said elongated member.

9. An apparatus according to claim 7, wherein said depressing means further includes flexing means, said flexing means being located external said housing means and entering into said housing means for flexing said elongated member.

10. An apparatus according to claim 9, wherein said flexing means includes a lever arm having one end pivotally coupled to said housing means and a second end that enters through an aperture in said housing means and abuts against said elongated member, whereby moving said lever arm towards said housing means causes said elongated member to flex.

11. An apparatus according to claim 10, wherein said lever arm is L-shaped.

12. An apparatus according to claim 10, wherein said flexing means includes a push button, said push button having one end that enters through said aperture in said housing means and is connected to said elongated member and a second end external said housing means at said aperture, whereby moving said push button towards said housing means causes said elongated member to flex.

13. An apparatus according to claim 10, wherein an end of said housing means opposite said exterior surface is open and receives covering means for covering said open end of said housing means, wherein said first end of said elongated member is pivotally attached to a first end of said covering means, and wherein said one end of said lever arm is pivotally attached to said covering means.

14. An apparatus according to claim 13, further including a reference member having one end attached to a second end of said covering means, and wherein said living hinge pivotally attaches said first end of said blade pivoting means to an opposite end of said reference member, said reference member and said covering means functioning to separate said blade pivoting means and said elongated member by a predetermined distance, that allows said second end of said elongated member to coact with said sloped surface of said blade pivoting means.

15. An apparatus according to claim 14, wherein said lever arm, said blade pivoting means, said elongated member, said covering means and said reference member are integrally formed.

16. An apparatus according to claim 1, wherein said blade pivoting means further includes actuatable retracting means for rapidly retracting said blade, said depressing means actuating said retracting means immediately after traversing said sloped surface of said blade pivoting means, whereby said cutting edge implements a skin incision and then immediately retracts into said housing means.

17. An apparatus according to claim 16, wherein said depressing means further includes locking means for locking said elongated member to said blade pivoting means after said blade retracts into said housing means.

18. An apparatus according to claim 16, wherein said retracting means includes an elongated projection, located intermediate said first and second ends of said blade pivoting means, and wherein said depressing means strikes said elongated projection immediately after traversing said sloped surface and urges said blade pivot means to pivot said blade into said housing means.

19. An apparatus according to claim 1, wherein said blade pivoting means further includes a first living hinge that pivotally couples said first end of said blade pivot means to said housing means, wherein said first living hinge urges said blade pivot means to pivot said cutting edge into said housing means after said depressing means traverses said sloped surface of said blade pivoting means.

20. An apparatus according to claim 18, wherein said second end of said elongated member terminates in a first leg and a second leg, said first leg traversing said sloped surface of said blade pivoting means when said depressing means is actuated, and said second leg coacting with said elongated projection after said first leg traverses said sloped surface.

21. An apparatus according to claim 20, wherein said blade pivoting means further includes engaging means located at said second end of said blade pivoting means for engaging said first leg of said elongated member.

22. An apparatus according to claim 20, wherein said depressing means includes a second living hinge, for coupling said first end of said elongated member to said housing means and for urging said elongated member against said sloped surface of said blade pivoting means, and a notch located on said elongated member for receiving the tip of said sloped surface, which notch receives the tip of said sloped surface after said second leg strikes said elongated projection, whereby said blade is locked entirely in said housing means.

23. Apparatus for implementing a skin incision, comprising:

a blade having a cutting edge;

housing mean for housing said blade, said housing means having a surface adapted to be placed flush against the skin and an elongated slot on said surface;

blade pivoting means, located within said housing means, for pivotally guiding said blade through said elongated slot, said blade pivoting means having a first and second end wherein said first end is pivotally coupled to said housing means and said second end supports said blade, whereby said cutting edge extends from a first surface of said second end toward said elongated slot, said second end having a sloped surface formed thereon, opposite said first surface;

actuatable depressing means, located within said housing means, and when actuated enabling said depressing means to traverse said sloped surface, displacing said second end of said blade pivoting means toward said elongated slot, such that said cutting edge of said blade emerges from said elongated slot and incises the skin; and retracting means, positioned on said blade pivoting means, for rapidly retracting said second end of said blade pivoting means when coacted by said depressing means immediately after traversing said sloped surface of said second end of said blade pivoting means such that said cutting edge of said blade is retracted from said elongated slot into said housing means.

* * * * *